(12) United States Patent
Ichijo (10) Patent No.: US 6,636,307 B2
(45) Date of Patent: Oct. 21, 2003

(54) LIGHT SCATTERING TYPE PARTICLE DETECTOR

(75) Inventor: Kazuo Ichijo, Tokyo (JP)

(73) Assignee: Rion Co., LTD, Tokyo (JP)

( * ) Notice: Subject to any disclaimer, the term of this patent is extended or adjusted under 35 U.S.C. 154(b) by 0 days.

(21) Appl. No.: 09/852,964

(22) Filed: May 10, 2001

(65) Prior Publication Data
US 2002/0030815 A1 Mar. 14, 2002

(30) Foreign Application Priority Data
May 12, 2000 (JP) ........................................ 2000-140255
Apr. 27, 2001 (JP) ........................................ 2001-133432

(51) Int. Cl.[7] .............................................. G01N 15/02
(52) U.S. Cl. ....................................... 356/336; 356/337
(58) Field of Search ................................ 356/336, 337, 356/339

(56) References Cited

U.S. PATENT DOCUMENTS

| | | | | |
|---|---|---|---|---|
| 4,798,465 A | * | 1/1989 | Knollenberg | 356/336 |
| 5,007,737 A | * | 4/1991 | Hirleman, Jr. | 356/336 |
| 5,576,827 A | * | 11/1996 | Strickland et al. | 356/336 |
| 5,737,078 A | * | 4/1998 | Takarada et al. | 356/338 |
| 5,754,291 A | * | 5/1998 | Kain | 356/338 |

* cited by examiner

*Primary Examiner*—Hung Xuan Dang
(74) *Attorney, Agent, or Firm*—Carrier, Blackman & Associates, P.C.; Joseph P. Carrier; William D. Blackman (57) ABSTRACT

A light scattering type particle detector in which the S/N ratio is improved includes a particle detecting region D which is formed by irradiating laser light La on sample fluid and a light receiving array 5 which receives scattering light Ls due to particles which pass through the particle detecting region. The light receiving array 5 is formed to be circular by arranging a plurality of photoelectric converters Pd1–Pdn in a plane alignment. The particle detector also includes an adder 6 which adds the output from the plurality of the photoelectric converters Pd1–Pdn.

24 Claims, 5 Drawing Sheets

LIGHT SCATTERING TYPE PARTICLE DETECTOR

BACKGROUND OF THE INVENTION

1. Field of the Invention

The present invention relates to a light scattering type particle detector for detecting particles, which pass through a particle detecting region, by receiving light scattered by the particles.

2. Description of the Prior Art

The S/N ratio (signal-to-noise ratio) of the electric signal output by a photoelectric converter which receives scattering light depends on the amount of shot noise in the photoelectric converter. The amount of the shot noise is proportional to the light amount incident upon the photoelectric converter.

Therefore, in a case where background light (background molecule scattering light) is large, the shot noise in the photoelectric converter is increased, and thereby the S/N ratio is deteriorated.

The background light means scattering light which occurs due to molecules of medium (for example, fluid such as air or liquid) containing particles to be measured, or due to the wall surface of a flow cell for passing fluid therethrough. For example, there are $2.7 \times 10^{19}$ air molecules per 1 ml at the atmosphere. The total amount of the light scattered by such molecules is larger than that of a 0.1 μm size particle.

Therefore, the larger the particle detecting region becomes, the more difficult it becomes to detect a particle. In addition, it is required to control smaller particles in a clean room for semiconductors because the level of its cleanness is improved and the concentration of particles is reduced.

A particle size detecting apparatus described in Japanese Patent No. 2786187 is known as a light scattering type particle detector for solving the above-mentioned problems.

Figure 5:
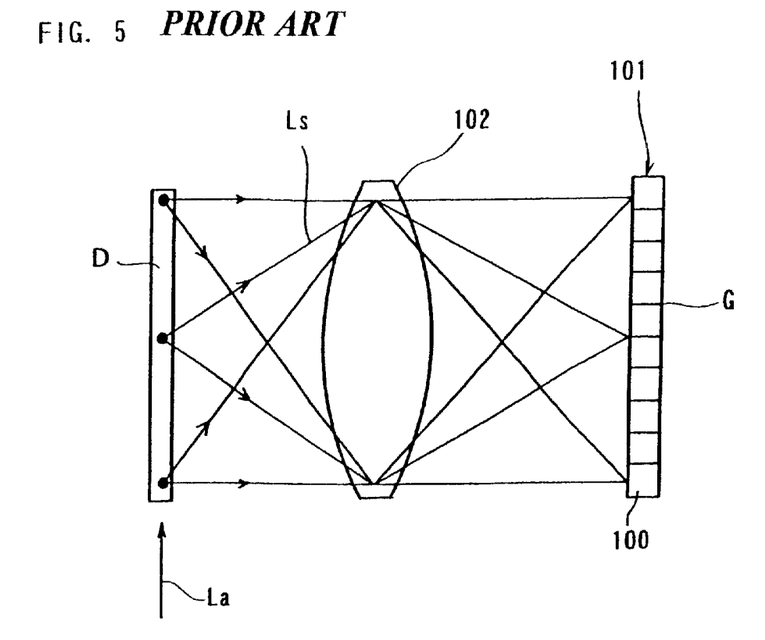
FIG. 5 is a view showing the structure of a light scattering type particle detector according to the prior art.

In this apparatus, as shown in FIG. 5, a light receiving array 101 comprising a plurality of photoelectric converters 100 in a linear alignment is used for receiving light. The scattering light Ls due to particles passing through the particle detecting region D is focused on one of the photoelectric converters 100 with the condenser lens 102. The background light incident upon the photoelectric converter 100, on which the scattering light Ls is focused, is reduced by the number of the photoelectric converters 100, and thereby the deterioration of the S/N ratio in the photoelectric converter 100, on which the scattering light Ls is focused, is prevented.

However, the apparatus as shown in FIG. 5 has the following problems:

1. When the number of the photoelectric converters 100 is increased, the S/N ratio can be improved. However, in a case where the photoelectric converters 100 are arranged in a linear, i.e., one-dimensional alignment, the finite light receiving area puts limitations on increasing the number of the photoelectric converters 100.

Figure 6:
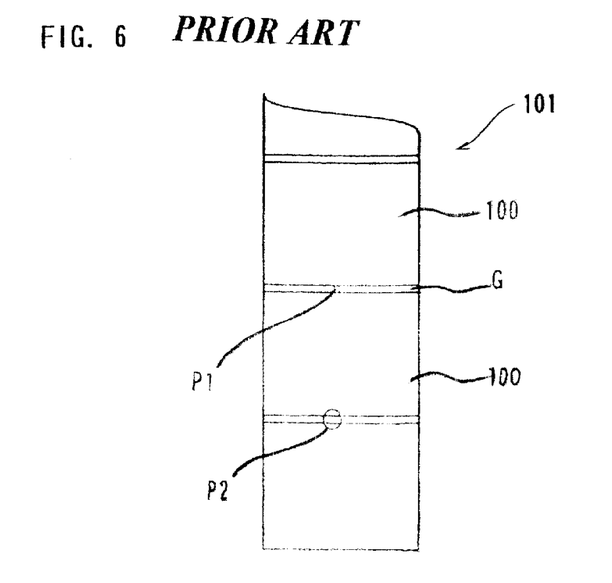
FIG. 6 is a front view of the light receiving array showing the condition of receiving light in a light scattering type particle detector according to the prior art.

It is preferable that the width of the gap G between the photoelectric converters be as small as possible. However, in fact, the width of the gap G has its limits. If the number of the photoelectric converters 100 is increased in the finite light receiving area, the ratio of the gap G to the light receiving area is too large, and thereby the accurate measurement is blocked. For example, as shown in FIG. 6, there is a case where the scattering light Ls due to a particle is focused on the gap G as an image P1. In this case, it is impossible to detect the particle.

2. As also shown in FIG. 6, if there is a bit of aberration in the condenser lens 102, the scattering light Ls due to a particle may be focused on the photoelectric condensers 100 adjacent each other sandwiching the gap G as an image P2. In this case, the particle may be detected as two particles or a smaller particle than its reality.

SUMMARY OF THE INVENTION

It is therefore an object of the present invention to solve these problems found in the prior art and to provide a light scattering type particle detector in which the S/N ratio is improved.

According to the first aspect of the present invention, there is provided a light scattering type particle detector for detecting particles comprising a particle detecting region formed by irradiating a light beam on sample fluid and a light receiving means for receiving light scattered by particles which pass through the particle detecting region, wherein the light receiving means is comprised of a plurality of photoelectric converters, and an add processing means is provided for conducting an add processing of the output from the plurality of photoelectric converters.

According to the second aspect of the present invention, the detector of the first aspect further comprises a condenser lens, having a sufficiently large aperture with respect to the particle detecting region, placed between the particle detecting region and the plurality of photoelectric converters, wherein the particle detecting region is adjusted to the focal point of the condenser lens, the scattering light due to particles is collimated with the condenser lens, and the collimated light is made incident upon the plurality of photoelectric converters.

According to the third aspect of the present invention, the detector of the first aspect further comprises a concave mirror, having a sufficiently large aperture with respect to the particle detecting region, placed in the position opposite to the plurality of photoelectric converters with the particle detecting region being therebetween, wherein the particle detecting region is adjusted to the focal point of the concave mirror, the scattering light due to particles is collimated with the concave mirror, and the collimated light is made incident upon the plurality of photoelectric converters.

According to the fourth aspect of the present invention, in the above-mentioned detector, the plurality of photoelectric converters are arranged in a linear or plane alignment.

BRIEF DESCRIPTION OF THE DRAWINGS

The above and other objects, features and advantages of the present invention will become more apparent from the following description when taken in conjunction with the accompanying drawings.

DETAILED DESCRIPTION OF THE PREFERRED EMBODIMENTS

Preferred embodiments of the present invention will now be described with reference to the accompanying drawings.

Figure 1:
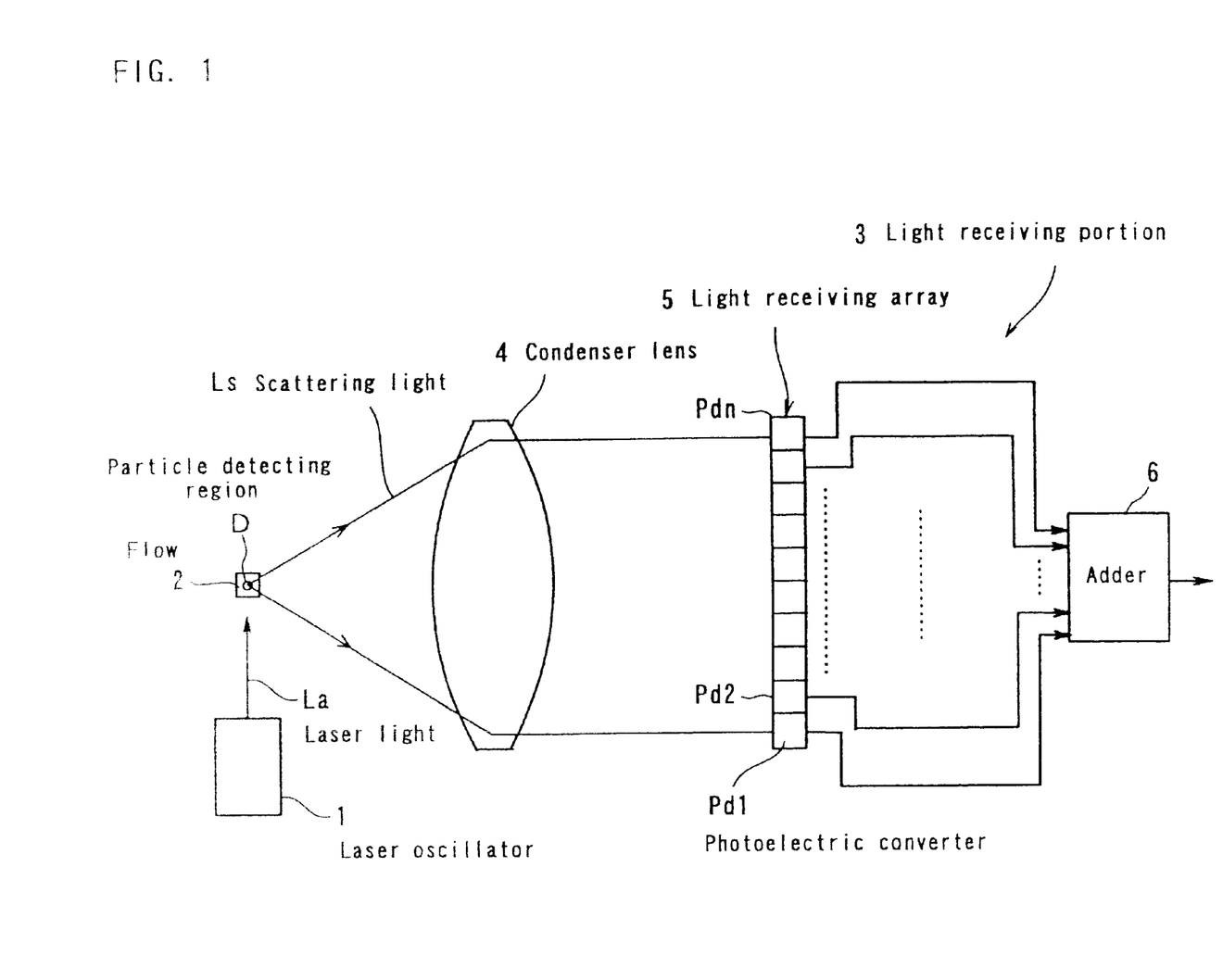
FIG. 1 is a view showing the structure of the first embodiment of a light scattering type particle detector according to the present invention.

The first embodiment of a light scattering type particle detector according to the present invention, as shown in FIG. 1, is comprised of a laser oscillator 1 for emitting laser light La as a light source, a flow 2 to be measured, and a light receiving portion 3 for receiving scattering light Ls.

The flow 2 is defined by passing fluid, which contains particles to be measured, from an inlet to an outlet by means of a suction pump (not shown), which is connected to the downstream of the outlet, for sucking the fluid. The particle detecting region D is the region where the laser light La and the flow 2 intersect. The flow 2 may be formed by passing fluid through a flow cell.

Further, the light receiving portion 3 is comprised of a condenser lens 4 for collimating the scattering light Ls generated in the particle detecting region D, a light receiving array 5 for photoelectrically converting the scattering light ls collimated with the condenser lens 4, and an adder 6 for adding the output from the light receiving array 5.

The condenser lens 4 has a sufficiently large aperture with respect to the particle detecting region D. The particle detecting region D is adjusted to the focal point of the condenser lens 4.

Therefore, the scattering light Ls due to particles in the particle detecting region D is collected with the condenser lens 4 to be substantially parallel light and is made incident upon the light receiving array 5.

Figure 2:
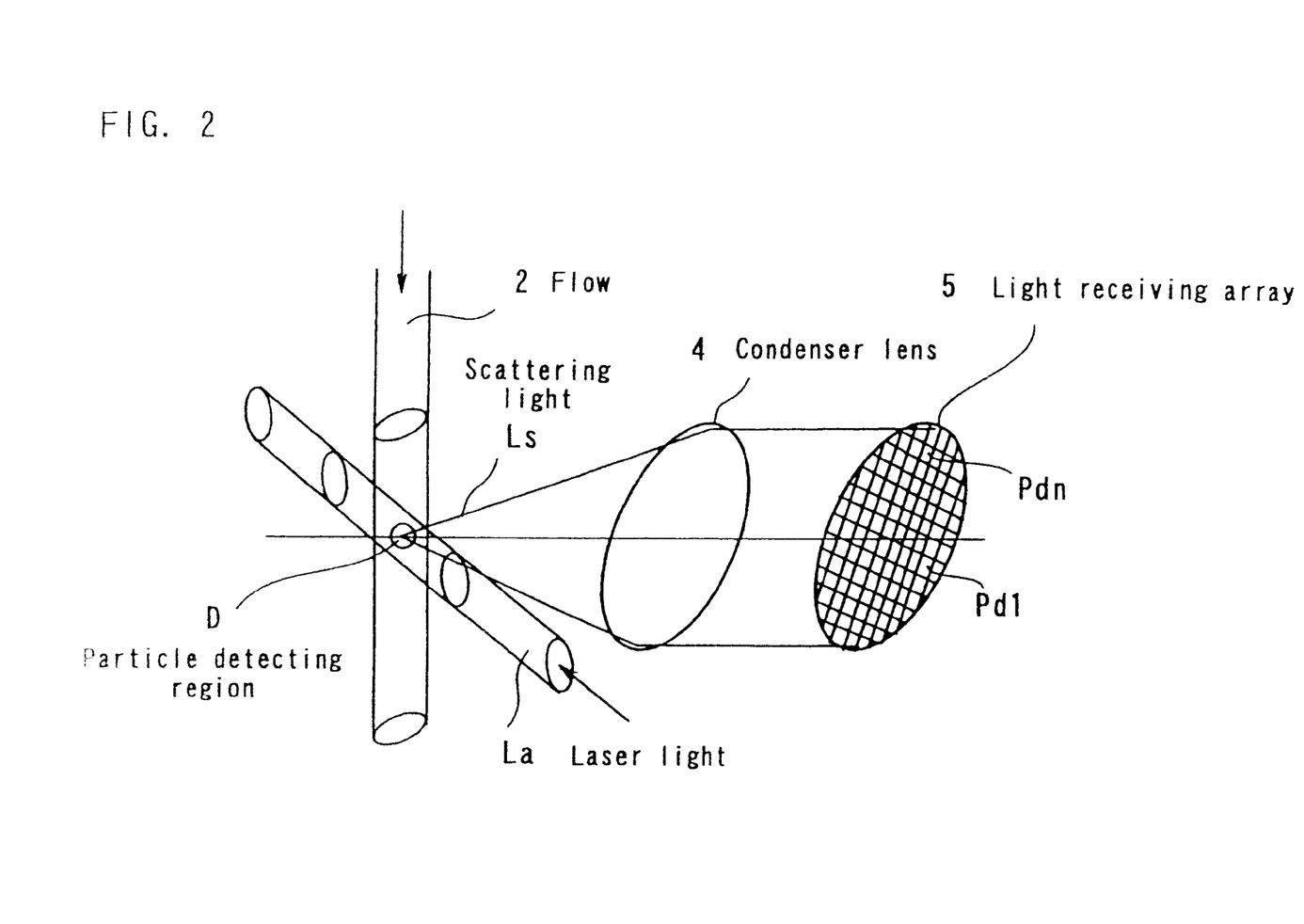
FIG. 2 is a view showing the concept of the present invention.

The light receiving array 5 as shown in FIG. 2, is formed to be circular by arranging n pieces of photoelectric converters Pd1–Pdn in a plane alignment. The photoelectric converters Pd1–Pdn receive the scattering light Ls, which is generated by particles irradiated with the laser light La in the particle detecting region D, via the condenser lens 4, photoelectrically convert the scattering light Ls, an output an electric signal (voltage) in accordance with the intensity of the scattering light Ls. In this case, the light receiving array 5 receives the scattering light Ls via the condenser lens 4 through the entire light receiving surface of the n pieces of photoelectric converters Pd1–Pdn, i.e., the surface of the photoelectric converters Pd1–Pdn facing toward the lens 4.

The adder 6 adds the voltage output from the photoelectric converters Pd1–Pdn, and outputs the added voltage.

The voltage output from the photoelectric converters Pd1–Pdn includes voltage based on the scattering light Ls and voltage based on the noise. When the voltage output from the photoelectric converters Pd1–Pdn based on the scattering light Ls is respectively expressed by $Es1, Es2, \ldots Esn$ and the voltage output from the photoelectric converters Pd1–Pdn based on the noise is respectively expressed by $En1, En2, \ldots Enn$, the output voltage E from the adder 6 can be expressed by the following equation (1):

$$E = (Es1 + Es2 + \ldots + Esn) + (En1^2 + En2^2 + \ldots + Enn^2)^{1/2} \quad (1)$$

In equation (1), the voltage $Es1, Es2, \ldots Esn$ based on the scattering light ls are simply added. On the other hand, the voltage $En1, En2, \ldots Enn$ based on the noise is respectively squared, the squared values are added, and the square root of the added value is obtained.

The reason is because the voltage $Es1, Es2, \ldots Esn$ based on the scattering light Ls are temporally synchronous and the voltage $En1, En2, \ldots Enn$ based on the noise are not temporally synchronous.

The S/N ratio in the output voltage E from the adder 6 can be expressed by the following equation (2):

$$S/N = (Es1 + Es2 + \ldots + Esn)/(En1^2 + En2^2 + \ldots + Enn^2)^{1/2} \quad (2)$$

If each of the voltage $Es1, Es2, \ldots Esn$ based on the scattering light Ls is 1 volt and each of the voltage $En1, En2, \ldots Enn$ based on the noise is also 1 volt, the S/N ratio can be expressed by the following equation (3):

$$S/N = n/n^{1/2} = n^{1/2} \quad (3)$$

Equation (3) shows that the S/N ratio in the light scattering type particle detector can be improved by increasing the number n of the photoelectric converters.

As explained above, according to the first embodiment of the present invention, the light receiving array 5 comprising the n pieces of photoelectric converters Pd1–Pdn receives the scattering light Ls generated in the particle detecting region D with the condenser lens 4 through the entire light receiving surface of the n pieces of photoelectric converters Pd1–Pdn. The voltage output from the photoelectric converters Pd1–Pdn are added with the adder 6. Therefore, the S/N ratio can be improved under no influence of the gap G between the photoelectric converters 100. It is possible to realize a highly accurate apparatus by applying a light scattering type particle detector of the present invention to a particle counting apparatus, a particle diameter distribution measurement apparatus, or the like.

Figure 3:
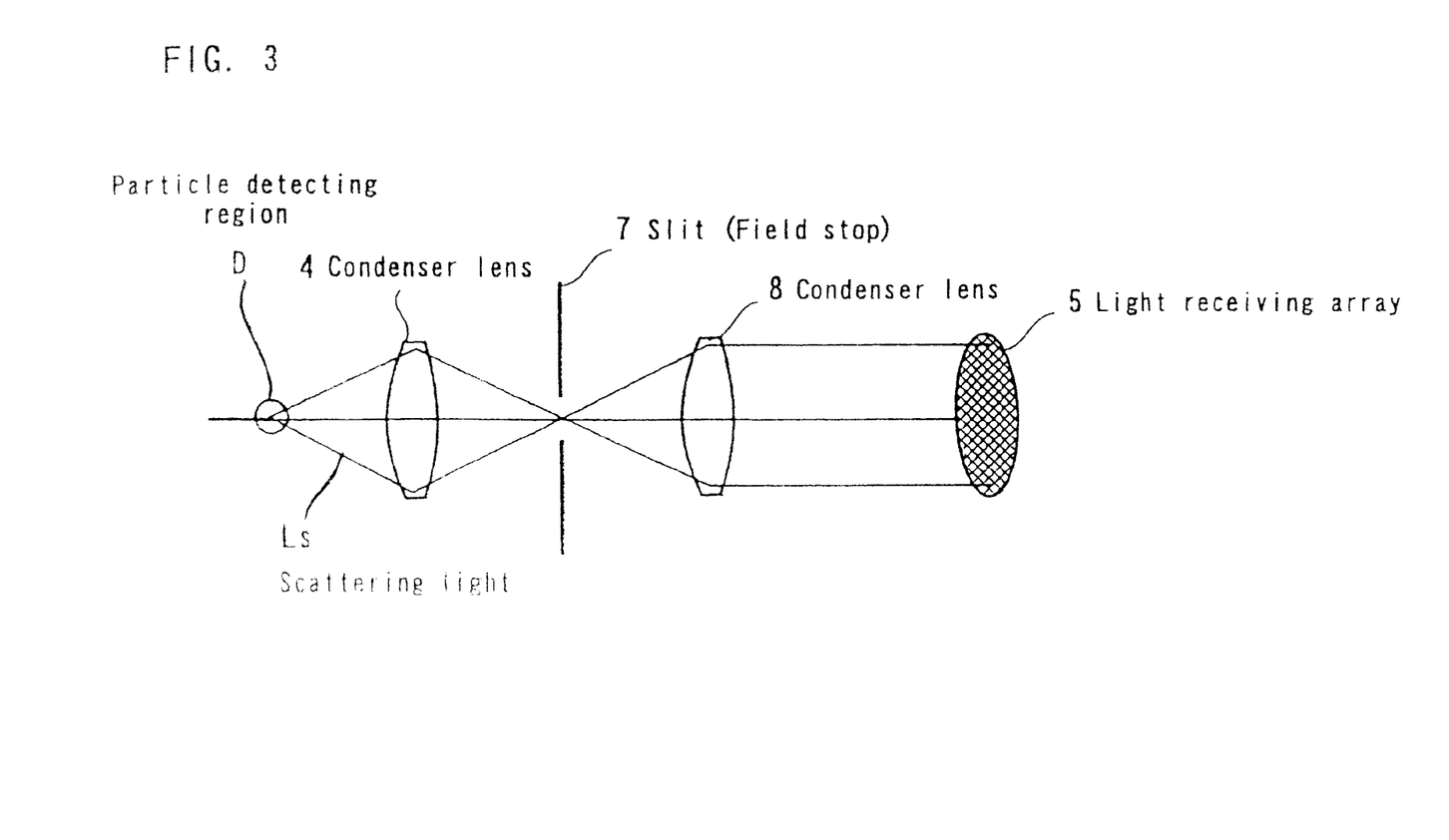
FIG. 3 is a view showing the structure of the first embodiment in which a field stop is provided.

Also, as shown in FIG. 3, slit (field stop) 7 and another condenser lens 8 may be provided between the condenser lens 4 and the light receiving array 5 in order to prevent background light generated some here else than in the particle detecting region D from being incident upon the light receiving array 5.

Figure 4:
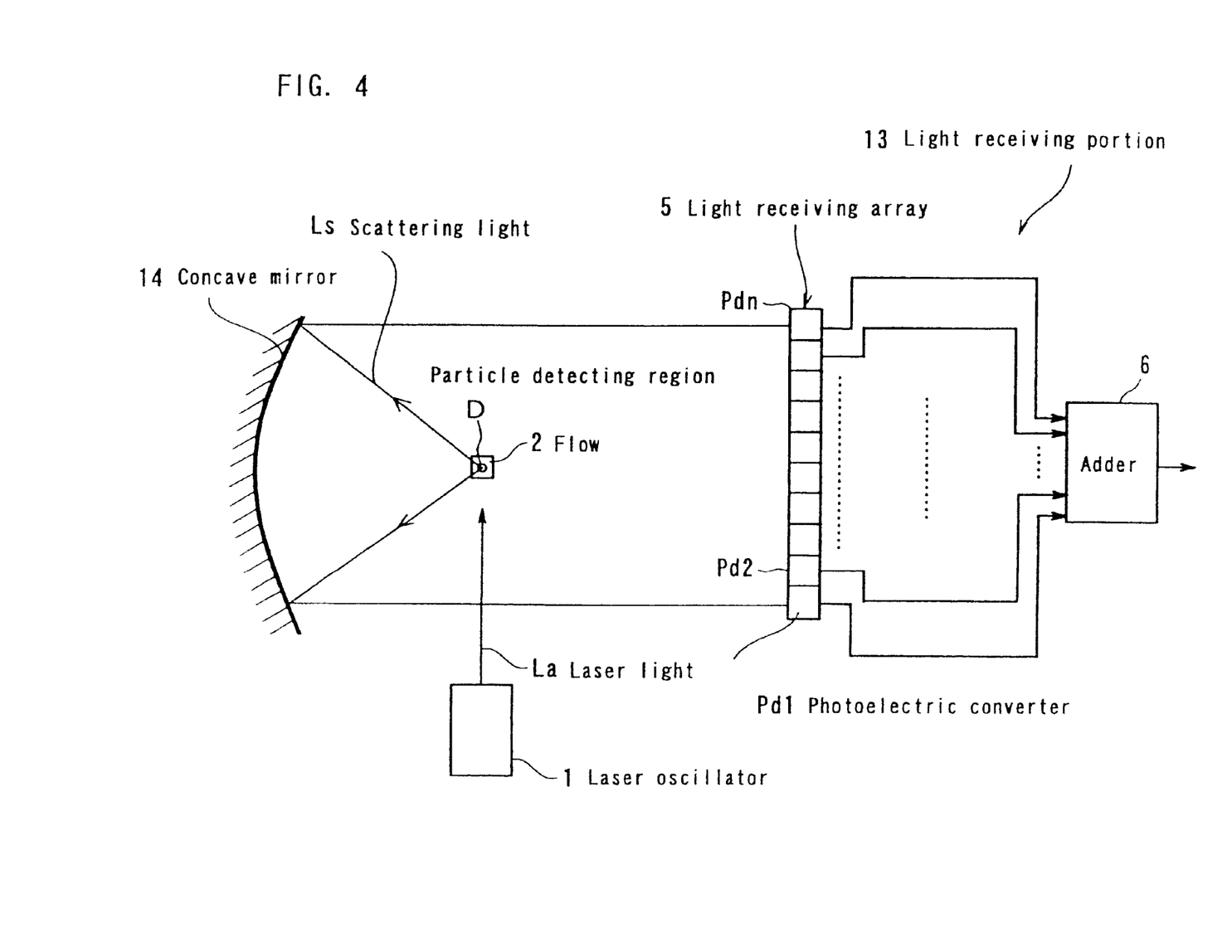
FIG. 4 is a view showing the structure of the second embodiment of a light scattering type particle detector according to the present invention.

The second embodiment of a light scattering type particle detector according to the present invention, as shown in FIG. 4, is comprised of a laser oscillator 1 for emitting laser light La as a light source, a flow 2 to be measured, and a light receiving portion 13 for receiving scattering light Ls.

Further, the light receiving portion 13 is comprised of a concave mirror 14 for collimating the scattering light Ls generated in the particle detecting region D, a light receiving array 5 for photoelectrically converting the scattering light Ls collimated with the concave mirror 14, and an adder 6 for adding the output from the light receiving array 5. An explanation of the elements having the same reference number as in FIG. 1 is omitted.

The concave mirror 14 has a sufficiently large aperture with respect to the particle detecting region D and has a parabolic shape. The particle detecting region D is adjusted to the focal point of the concave mirror 14.

The particle detecting region D is located between the concave mirror 14 and the light receiving array 5. The scattering light Ls due to particles in the particle detecting region D is collected with the concave mirror 14 to be substantially parallel light and is made incident upon the light receiving array 5.

The light receiving array 5 photoelectrically converts the scattering light Ls, and outputs an electric signal (voltage) in accordance with the intensity of the scattering light Ls. In this case, the light receiving array 5 receives the scattering light Ls via the concave mirror 14 through the entire light receiving surface of the array, i.e., the surface of the photoelectric converters Pd1–Pdn facing toward the mirror 14.

The adder 6 adds the voltage output from the photoelectric converters Pd1–Pdn, and outputs the added voltage. The subsequent signal processing is the same as in the first embodiment.

As explained above, according to the second embodiment of the present invention, the light receiving array 5 comprising the n pieces of photoelectric converters Pd1–Pdn receives the scattering light Ls generated in the particle detecting region D with the concave mirror 14 through the entire light receiving surface of the n pieces of photoelectric converters Pd1–Pdn. The voltage output from the photoelectric converters Pd1–Pdn are added with the adder 6. Therefore, the S/N ratio can be improved under no influence of the gap G between the photoelectric converters 100. It is possible to realize a highly accurate apparatus by applying a light scattering type particle detector of the present invention to a particle counting apparatus, a particle diameter distribution measurement apparatus, or the like.

In the above-mentioned embodiments, the light receiving array 5 is formed to be circular by arranging the photoelectric converters Pd1–Pdn in a plane (two-dimensional) alignment. The light receiving array 5 may be form by arranging the photoelectric converters in a linear (one-dimensional) alignment. However, the S/N ratio can be more improved in the case of arranging a plane alignment rather than a linear alignment because the plane alignment enables use of an increased number of the photoelectric converters.

As described above, according to the first aspect of the present invention, since the scattering light is received and photoelectrically converted with the plurality of photoelectric converters and the output from the photoelectric converters are added, it is possible to improve the S/N ratio under no influence of the gap between the photoelectric converters.

According to the second aspect of the present invention, since the scattering light is collimated with the condenser lens so that the scattering light is incident upon the entire surface area of the photoelectric converters facing toward the lens and the outputs from the photoelectric converters are added, it is possible to improve the S/N ratio.

According to the third aspect of the present invention, since the scattering light is collimated with the concave mirror so that the scattering light is incident upon the entire surface area of the photoelectric converters facing toward the mirror and the outputs from the photoelectric converters are added, it is possible to improve the S/N ratio.

According to the fourth aspect of the present invention, since the scattering light is made incident upon the plurality of photoelectric converters arranged in a linear or plane alignment and the output from the photoelectric converters are added, it is possible to improve the S/N ratio.

Although there have been described in detail what are the present embodiments of the invention, it will be understood by persons skilled in the art that variations and modifications may be made thereto without departing from the gist, spirit or essence of the invention as reflected in the appended claims.

What is claimed is:

1. A light scattering type particle detector for detecting particles comprising:
   a particle detecting region formed by irradiating a light beam on fluid sample; and
   a light receiving means fort receiving light scattered by particles which pass through said particle detecting region,
   wherein said light receiving means is comprised of a condenser means, a plurality of photoelectric converters, and an add processing means provided for conducting an add processing of the output from said plurality photoelectric converters, and
   wherein said light scattered by particles is collimated with said condenser means.

2. A light scattering type particle detector as defined in claim 1, wherein said condense means comprises a condenser lens, having a sufficiently large aperture with respect to said particle detecting region, placed between said particle detecting region and said plurality of photoelectric converters,
   wherein said particle detecting region is adjusted to the focal point of said condenser lens, the scattered light due to particles is collimated with said condenser lens, and the collimated light is made incident upon said plurality of photoelectric converters.

3. A light scattering type particle detector as defined in claim 1, wherein said condenser means comprises a concave mirror, having a sufficiently large aperture with respect to said particle detecting region, placed in the position opposite to said plurality of photoelectric converters with said particle detecting region being therebetween,
   wherein said particle detecting region is adjusted to the focal point of said concave mirror, the scattered light due to particles is collimated with said concave mirror, and the collimated light is made incident upon said plurality of photoelectric converters.

4. A light scattering type particle detector as defined in any one of claims 1, 2 and 3, wherein said plurality of photoelectric converters are arranged in a linear or plane alignment.

5. A light scattering type particle detector as defined in claim 1, wherein said plurality of photoelectric converters are arranged adjacent to each other in a planar alignment.

6. A light scattering type particle detector as defined in claim 1, wherein said plurality of photoelectric converters are arranged adjacent to each in a substantially circular, planar alignment.

7. A light scattering type particle detector as defined in claim 1, further including a field stop which restricts light other than scattered light from the particle detecting region from becoming incident upon said plurality of photoelectric converters.

8. A light scattering type particle detector as defined in claim 1, further including a collimating device which collimates said light scattered by particles passing through said particle detecting region before the scattered light is received by said light receiving means, and wherein said photoelectric converters receive the collimated, scattered light on the entire surface area of the photoelectric converters facing the collimating device.

9. A light scattering type particle detector as defined in claim 1, further including a flow cell, said sample fluid in said particle detecting region is disposed within said flow cell.

10. A light scattering type particle detector as defined in claim 1, wherein said add processing means add processes aid output signals of all of said photoelectric converters.

11. A light scattering type particle detector as defined in claim 1, wherein said add processing means add processes aid output signals of said photoelectric converters based on scattered light from said particle detecting region and noise.

12. A light scattering type particle detector comprising;
   a particle detecting region which a light beam is irradiated on a fluid sample;

a plurality of photoelectric converters which receive light scattered by particles passing through said particle detecting region and output corresponding signals;

an adder which add processes said output signals of substantially all of said photoelectric converters; and a collimating device which collimates said light scattered by particles passing through said particle detecting region before the scattered light is received by said plurality of photoelectric converters.

13. A light scattering type particle detector as defined in claim 12, wherein said collimating device comprises condenser lens, having a sufficiently large aperture with respect to said particle detecting region, placed between said particle detecting region and said plurality of photoelectric converters.

14. A light scattering type particle detector as defined in claim 11, wherein said particle detecting region is adjusted to the focal point of said condenser lens.

15. A light scattering type particle detector as defined in claim 12, wherein said collimating device comprises a concave mirror, having a sufficiently large aperture with respect to said particle detecting region, placed in a position opposite to said plurality of photoelectric converters with said particle detecting region disposed therebetween.

16. A light scattering type particle detector as defined in claim 15, wherein said particle detecting region is adjusted to the focal point of said concave mirror.

17. A light scattering type particle detector as defined in claim 12, wherein said plurality of photoelectric converters receive said scattered light on the entire surface area of the photoelectric converters facing toward the particle detecting region.

18. A light scattering type article detector as defined in claim 12, wherein said plurality of photoelectric converters are arranged adjacent to each other in a planar alignment.

19. A light scattering type particle detector as defined in claim 12, wherein said plurality of photoelectric converters are arranged adjacent to each in a substantially circular, planar alignment.

20. A light scattering type particle detector as defined in claim 12, further including a field stop which restricts light other than scattered light from the particle detecting region from becoming incident upon said plurality of photoelectric converters.

21. A light scattering type particle detector as defined in claim 12, wherein said adder add processes said output signals of said photoelectric converters based on scattered light from said particle detecting region and noise.

22. A light scattering particle detector as defined in claim 12, wherein said adder add processes said output signals of said photoelectric converters such that a signal-to-noise ratio is improved without influence of gaps existing between adjacent ones of said photoelectric converters.

23. A light scattering type particle detector as defined in claim 12, wherein said adder add processes said output signals of said photoelectric converters to establish an output voltage E according to the equation:

$$E=(Es1, +Es2+ \ldots +Esn)+(En1^2+En2^2 + \ldots +Enn^2)^{1/2},$$

where $Es1, +Es2+ \ldots + Esn$ represent respective voltage outputs from the photoelectric converters based on scattered light, and $Es1, +Es2+ \ldots + Esn$ represent respective voltage outputs from the photoelectric converters based on noise.

24. A light scattering type particle detector for detecting particles comprising:

a particle detecting region formed by irradiating a light beam on fluid sample; and a light receiving means for receiving light scattered by particles which pass through said particle detecting region, wherein said light receiving means is comprised of a plurality of photoelectric converters, and an add processing means for conducting an add processing of the output from said plurality photoelectric converters, and said add processing means add processes said output signals of said photoelectric converters such that a signal-to-noise ratio is improved without influence of gaps existing between adjacent ones of said photoelectric converters.

* * * * *

UNITED STATES PATENT AND TRADEMARK OFFICE
CERTIFICATE OF CORRECTION

PATENT NO. : 6,636,307 B2
APPLICATION NO. : 09/852964
DATED : October 21, 2003
INVENTOR(S) : Kazuo Ichijo It is certified that error appears in the above-identified patent and that said Letters Patent is hereby corrected as shown below:

Title Page:
   In the "(57) ABSTRACT", 6th line, change
"region. The light receiving array 5 is formed to be circular" to
--region D. The light receiving array 5 is formed to be circular--.

Column 3:
   Line 27, change
"array 5 for photoelectrically converting the scattering light Is" to
--array 5 for photoelectrically converting the scattering light $L_s$--.
   Line 37, change
"upon the light receiving array 5." to
--upon the light receiving array 5. As will be understood, the condenser lens 4 functions as a condenser means for collimating the light scattered by the particles.--.
   Line 38, change
"The light receiving array 5 as shown in FIG. 2, is formed" to
--The light receiving array 5, as shown in FIG. 2, is formed--.
   Line 66, change
"scattering light Is are simply added. On the other hand, the" to
--scattering light $L_s$ are simply added. On the other hand, the--.

Column 4:
   Line 35, change
"Also, as shown in FIG. 3, slit (field stop) 7 and another" to
--Also, as shown in FIG. 3, a slit (field stop) 7 and another--.
   Line 38, change
"background light generated some here else than in the" to
--background light generated somewhere else than in the--.

Signed and Sealed this
Thirtieth Day of August, 2011

David J. Kappos
*Director of the United States Patent and Trademark Office*

CERTIFICATE OF CORRECTION (continued)
U.S. Pat. No. 6,636,307 B2

Column 4 (continued):
Line 63, change
"light receiving array 5." to
--light receiving array 5. As will be understood, the concave mirror 14 also functions as a condenser means for collimating the light scattered by the particles.--.

Column 5:
Line 24, change
"ment. The light receiving array 5 may be form by arranging" to
--ment. The light receiving array 5 may be formed by arranging--.
Line 64, change
"beam on fluid sample; and" to
--beam on sample fluid; and--.
Line 65, change
"a light receiving means fort receiving light scattered by" to
--a light receiving means for receiving light scattered by--.

Column 6:
Line 5, change
"plurality photoelectric converters, and" to
--plurality of photoelectric converters, and--.
Line 9, change
"claim 1, wherein said condense means comprises a con-" to
--claim 1, wherein said condenser means comprises a con- --.
Line 15, change
"focal point of said condenser lens, the scattered light" to
--focal point of said condenser lens, the scattering light--.
Line 26, change
"focal point of said concave mirror, the scattered light" to
--focal point of said concave mirror, the scattering light--.
Line 39, change
"are arranged adjacent to each in a substantially circular," to
--are arranged adjacent to each other in a substantially circular,--.
Line 60, change
"aid output signals of all of said photoelectric converters." to
--said output signals of all of said photoelectric converters.--.
Line 63, change
"aid output signals of said photoelectric converters based on" to
-- said output signals of said photoelectric converters based on--.
Line 65, change
"12. A light scattering type particle detector comprising;" to
--12. A light scattering type particle detector comprising:--.
Line 66, change
"a particle detecting region which a light beam is irradiated" to
--a particle detecting region in which a light beam is irradiated--.

Column 7:
   Line 11, change
"claim 12, wherein said collimating device comprises con-" to
--claim 12, wherein said collimating device comprises a con- --.
   Line 17, change
"claim 11, wherein said particle detecting region is adjusted" to
--claim 13, wherein said particle detecting region is adjusted--.
   Line 32, change
"18. A light scattering type article detector as defined in" to
--18. A light scattering type particle detector as defined in--.
   Line 36, change
"are arranged adjacent to each in a substantially circular," to
--are arranged adjacent to each other in a substantially circular,--.

Column 8:
   Line 35, change
"output from said plurality photoelectric converters, and" to
--output from said plurality of photoelectric converters, and--.
   Line 5, change
"22. A light scattering particle detector as defined in claim" to
--22. A light scattering type particle detector as defined in claim--.